US008834693B2

(12) United States Patent
Su et al.

(10) Patent No.: US 8,834,693 B2
(45) Date of Patent: Sep. 16, 2014

(54) GAS SENSOR ELEMENT AND GAS SENSOR INCLUDING THE SAME

(75) Inventors: Zhenzhou Su, Okazaki (JP); Kiyomi Kobayashi, Kuwana (JP); Motoaki Satou, Anjo (JP)

(73) Assignee: Denso Corporation, Kariya (JP)

( * ) Notice: Subject to any disclaimer, the term of this patent is extended or adjusted under 35 U.S.C. 154(b) by 451 days.

(21) Appl. No.: 12/645,757

(22) Filed: Dec. 23, 2009

(65) Prior Publication Data

US 2010/0163411 A1    Jul. 1, 2010

(30) Foreign Application Priority Data

Dec. 25, 2008   (JP) .................................. 2008-329086

(51) Int. Cl.
*G01N 27/407*   (2006.01)
(52) U.S. Cl.
CPC .................................. *G01N 27/4077* (2013.01)
USPC ........................... 204/429; 73/23.31; 73/23.32
(58) Field of Classification Search
CPC ................................................ G01N 27/4077
USPC .................. 204/421–429, 410, 411; 205/781, 205/783.5–785, 787; 73/23.31, 23.32
See application file for complete search history.

(56) References Cited

U.S. PATENT DOCUMENTS

| | | | | |
|---|---|---|---|---|
| 5,472,591 | A | * | 12/1995 | Saito et al. ..................... 204/429 |
| 5,538,612 | A | * | 7/1996 | Kojima et al. ................ 204/429 |
| 2001/0054553 | A1 | | 12/2001 | Isomura et al. |
| 2002/0060152 | A1 | * | 5/2002 | Hotta et al. .................... 204/429 |
| 2003/0061862 | A1 | | 4/2003 | Kondo et al. |
| 2004/0074072 | A1 | | 4/2004 | Iwata |

FOREIGN PATENT DOCUMENTS

| | | |
|---|---|---|
| JP | 56-090256 | 7/1981 |
| JP | 01-097855 | 4/1989 |
| JP | 11-072460 | 3/1999 |
| JP | 11-295263 | 10/1999 |
| JP | 2000-121597 | 4/2000 |
| JP | 2001-099806 | 4/2001 |
| JP | 2001-124725 | 5/2001 |
| JP | 2001-174434 | 6/2001 |

(Continued)

OTHER PUBLICATIONS

Japanese Office Action dated Oct. 26, 2010, issued in corresponding Japanese Application No. 2008-329086, with English Translation.

(Continued)

*Primary Examiner* — Jennifer Dieterle
(74) *Attorney, Agent, or Firm* — Nixon & Vanderhye P.C.

(57) ABSTRACT

The present invention provides, as one aspect, a gas sensor element including a solid electrolytic substance having a bottomed cylindrical shape and oxygen ion conductivity, a reference electrode arranged on an inner side surface of the solid electrolytic substance, a measuring electrode arranged on an outer side surface of the solid electrolytic substance, and a protective layer which covers the outer side surface of the solid electrolytic substance together with the measuring electrode and which allows gas to be measured to pass through the protective layer, wherein an end side of the gas sensor element is formed of a leg portion whose profile line is straight on an axial cross section and a bottom portion whose profile line is curved, and the film thickness of the protective layer of the bottom portion is larger than the film thickness of the protective layer of the leg portion.

7 Claims, 7 Drawing Sheets

(56) References Cited

FOREIGN PATENT DOCUMENTS

| JP | 2002-181769 | 6/2002 |
|----|-------------|--------|
| JP | 2003-107047 | 4/2003 |
| JP | 2004-138451 | 5/2004 |
| JP | 2006-038496 | 2/2006 |

OTHER PUBLICATIONS

Information Offer Form submitted Jan. 11, 2011 in corresponding Japanese Application No. 2008-329086, with English Translation.

* cited by examiner

GAS SENSOR ELEMENT AND GAS SENSOR INCLUDING THE SAME

CROSS REFERENCE TO RELATED APPLICATION

This application is based on and claims the benefit of priority from earlier Japanese Patent Application No. 2008-329086 filed Dec. 25, 2008, the description of which is incorporated herein by reference.

BACKGROUND OF THE INVENTION

1. Technical Field of the Invention

The present invention relates to a gas sensor element which detects a concentration of a specified gas to be measured and a gas sensor including the gas sensor element.

2. Related Art

Conventionally, a gas sensor element is known which includes a solid electrolytic substance having a bottomed cylindrical shape and oxygen ion conductivity, a reference electrode arranged on the inner side surface of the solid electrolytic substance, a measuring electrode arranged on the outer side surface of the solid electrolytic substance, and a protective layer which covers the outer side surface of the solid electrolytic substance together with the measuring electrode and allows gas to be measured to pass through the protective layer. (For example, refer to Japanese Patent Application Laid-open No. 2006-38496.)

Such a gas sensor element is formed of a leg portion whose profile line is straight on an axial cross section, which is parallel to the axis of the gas sensor element, and a bottom portion whose profile line is curved.

The above gas sensor element has problems as described below.

Since the bottom portion of the gas sensor element has low water resistance and strength, the bottom portion of the solid electrolytic substance is easily cracked when getting wet. The following reasons are assumed. First, the bottom portion of the solid electrolytic substance has a curved shape as described above, and thermal stress is easily concentrated in the bottom portion. Therefore, the bottom portion is easily cracked when getting wet. Second, water condensed when the car is stopping collects on the corners of a cover of the gas sensor element. The collected water easily contacts the bottom portion of the gas sensor element when the engine starts.

To solve the above problems, increasing the film thickness of the protective layer is assumed to improve the water resistance of the gas sensor element.

However, when the film thickness of the protective layer is simply increased, the following problems can arise. Since increasing the film thickness of the protective layer increases the amount of materials used for forming the protective layer and requires much time to spray the materials, the cost of manufacturing the gas sensor element can rise. In addition, when simply increasing the film thickness of the protective layer, rich components and lean components in the gas to be measured diffuse slowly to the measuring electrode. This can lower responsiveness of the gas sensor element.

SUMMARY OF THE INVENTION

The present invention has been made in consideration of the foregoing conventional situation, and an object of the present invention is to provide a gas sensor element and a gas sensor including the gas sensor element which can be manufactured at low cost and have excellent water resistance and responsiveness.

In order to achieve the object, the present invention provides, as one aspect, a gas sensor element including a solid electrolytic substance having a bottomed cylindrical shape and oxygen ion conductivity, a reference electrode arranged on an inner side surface of the solid electrolytic substance, a measuring electrode arranged on an outer side surface of the solid electrolytic substance, and a protective layer which covers the outer side surface of the solid electrolytic substance together with the measuring electrode and which allows gas to be measured to pass through the protective layer, wherein an end side of the gas sensor element is formed of a leg portion whose profile line is straight on an axial cross section, which is a cross section parallel to an axis of the gas sensor element, and a bottom portion whose profile line is curved, and the film thickness of the protective layer of the bottom portion is larger than the film thickness of the protective layer of the leg portion.

DETAILED DESCRIPTION OF THE PREFERRED EMBODIMENTS

Figure 1:
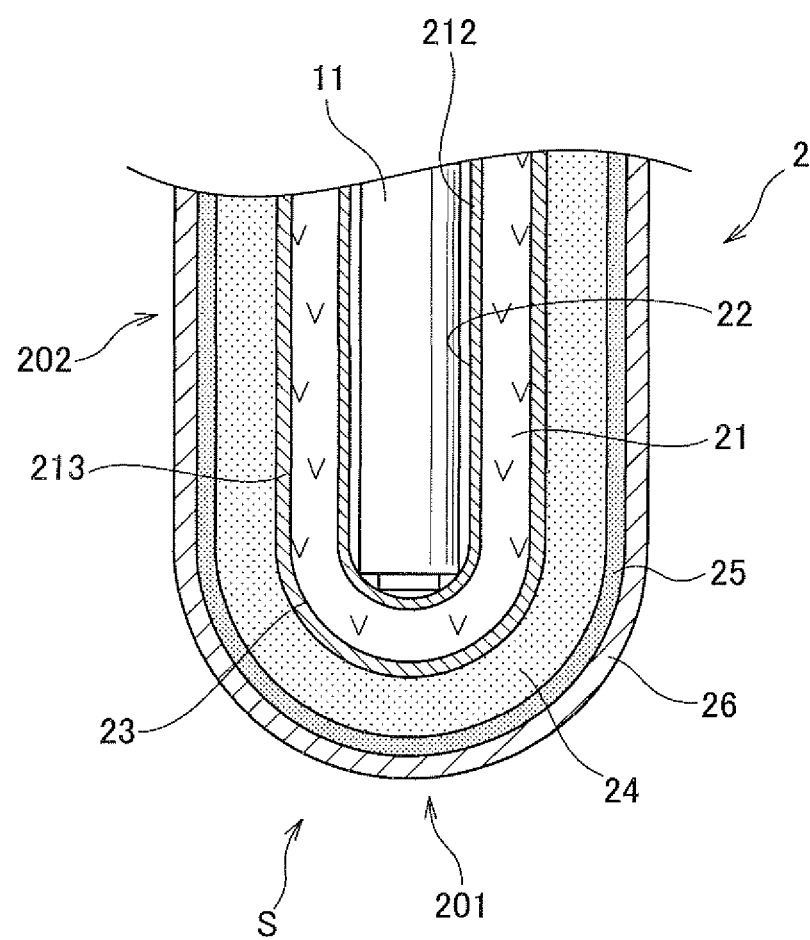
FIG. 1 is a sectional view of an end portion of a gas sensor element according to a first embodiment.

The gas sensor elements according to the embodiments include an air-fuel ratio sensor element which is disposed in an exhaust pipe of various internal combustion engines for vehicles and is used for an exhaust gas feedback system, and an oxygen sensor element, which measures a concentration of oxygen in exhaust gas.

In the present description, one side of a gas sensor which is inserted into, for example, an exhaust system of an internal combustion engine is referred to as an end side, and the opposite side of the end side is referred to as a base side.

In the present description, the film thickness of a bottom portion of a protective layer is a value obtained by averaging three film thicknesses when viewing an axial cross section of the gas sensor element. The first film thickness is a thickness of the protective layer at a position where an axis of the gas sensor element passes through the bottom portion. The second and third film thicknesses are thicknesses of the protective layer at two positions where lines pass through the bottom portion. Each of the lines is inclined at an angle of 30° with respect to the axis from the end side to the base side centering on a point where a boundary between the bottom portion and the leg portion and the axis intersect with each other (refer to FIG. 7).

The film thickness of the leg portion of the protective layer is a value obtained by averaging film thicknesses at three arbitrary points when viewing the axial cross section of the gas sensor element. The film thicknesses are thicknesses of the protective layer at the three points in an area, whose length is 5 mm, extending from the boundary between the bottom portion and the leg portion toward the base side (refer to FIG. 7).

In the protective layer, a film thickness ratio of the film thickness of the bottom portion to the film thickness of the leg portion is preferably 1.1 or more.

In this case, the film thickness of the protective layer of the bottom portion can be sufficiently larger than that of the leg portion. Therefore, the gas sensor element having high water resistance can be obtained.

Meanwhile, when the film thickness ratio is less than 1.1, the following problem arises. The amount of water in the gas to be measured varies depending on specifications of an engine, an exhaust pipe, and the like. Specifically, in a vehicle producing a large amount of water, the gas sensor element having a film thickness ratio of less than 1.1 can be difficult to obtain sufficient water resistance.

In addition, the film thickness ratio of the protective layer is preferably in the range of 1.2 to 2.

In this case, the gas sensor element having sufficiently high water resistance and sufficiently high responsiveness can be obtained. In addition, when the protective layer is formed by thermal spraying, the solid electrolytic substance can be prevented from cracking.

Conversely, when the film thickness ratio of the protective layer is less than 1.2, it can be difficult to improve water resistance sufficiently.

In addition, when the film thickness ratio of the protective layer is more than 2, the response time of the sensor becomes long at the bottom portion. Thereby, responsiveness of the gas sensor element can be lowered. In addition, when the protective layer is formed by thermal spraying, the solid electrolytic substance can be cracked.

In addition, in the protective layer, the film thickness of the leg portion is preferably in the range of 100 to 500 μm.

In this case, the gas sensor element can be obtained which has sufficient responsiveness as well as a function for protecting the electrodes by the protective layer.

Conversely, when the film thickness of the protective layer of the leg portion is less than 100 μm, the effect of limiting a flow rate of exhaust gas can be lowered. In consequence, when the gas sensor element is exposed to a high-temperature atmosphere for long periods of time, the measuring electrode can peel.

In addition, when the film thickness of the protective layer of the leg portion is more than 500 μm, the diffusion of the gas to the measuring electrode is delayed. This can lengthen response time of the sensor, which results in poor emission.

In addition, in the protective layer, a porosity of the bottom portion is preferably higher than that of the leg portion.

In this case, the gas sensor element can be obtained which maintains responsiveness and has excellent water resistance.

That is, according to the first embodiment, the film thickness of the protective layer of the bottom portion is larger than that of the leg portion, which improves water resistance and strength. However, in this case, the diffusion of the gas to be measured to the measuring electrode is delayed at the bottom portion, which can lower responsiveness of the gas sensor. To solve this problem, as described above, the porosity of the protective layer of the bottom portion whose film thickness is large is heightened. That is, in the protective layer, the porosity of the bottom portion is higher than that of the leg portion. This improves the diffusion of the gas at the bottom portion sufficiently, and maintains the responsiveness equivalent to that of a conventional gas sensor.

In consequence, the gas sensor element can be obtained which maintains responsiveness immediately after engine starting and has excellent water resistance.

In the description, the porosity of the protective layer of the bottom portion is a value obtained by averaging porosities at arbitrary three points in an area of the protective layer between two lines. Each of the lines is inclined at an angle of 30° with respect to the axis centering on a point where a boundary between the bottom portion and the leg portion and the axis intersect with each other.

The porosity of the protective layer of the leg portion is a value obtained by averaging porosities at arbitrary three points in an area, whose length is 5 mm, extending from the boundary between the bottom portion and the leg portion toward the base side.

More specifically, the porosity is a value obtained by taking images of the points magnified 400 times by an SEM (scanning electron microscope), then dividing the total of cross-sectional areas of pores existing in the SEM images by the total of areas of the SEM images.

In addition, in the protective layer, the porosity of the bottom portion is 50% or less, and a porosity ratio, which is a ratio of the porosity of the bottom portion to the porosity of the leg portion, is preferably in the range of 1.1 to 10.

In this case, the protective layer can be obtained which has sufficient strength as well as a function for protecting the electrodes. Furthermore, the gas sensor element can be obtained which has sufficient responsiveness.

Conversely, when the porosity of the protective film of the bottom portion is more than 50%, the strength of the protective layer is lowered. This can cause cracks in the protective layer, when using the gas sensor, and peeling of the protective layer.

In addition, when the porosity ratio is less than 1.1, specifically for a vehicle whose displacement is small, it can be difficult to obtain the gas sensor element having sufficient responsiveness because the gas flow rate is low.

Furthermore, when the porosity ratio is more than 10, the effect of restricting passing the gas to be measured by the protective layer is lowered, which can be difficult to obtain stable sensor outputs. In addition, peeling and deterioration of the measuring electrode can be accelerated.

In addition, the porosity ratio of the protective layer of the leg portion is preferably in the range of 2 to 20%.

In this case, the gas sensor element can be obtained which ensures responsiveness, produces outputs with stability, and has the effect of sufficiently restricting passing the gas to be measured.

Conversely, when the porosity ratio of the protective layer of the leg portion is less than 2%, the diffusion of the gas to the protective layer is significantly delayed, which can lower the responsiveness.

When the porosity ratio of the protective layer of the leg portion is more than 20%, the effect, by the protective layer, of restricting passing the gas to be measured is lowered, which becomes difficult to obtain stable sensor outputs. In addition, it becomes difficult to sufficiently restrict the diffusion of the gas. Thereby, the measuring electrode can be deteriorated early.

In addition, the protective layer is preferably formed of at least two layers.

In this case, the gas sensor element can be obtained which has excellent durability.

That is, densely constructing the lower most layer, which is included in the protective layer formed of at least two layers and contacts the measuring electrode, can control the diffusion of the gas to be measured, thereby obtaining a stable sensor characteristic, and can prevent the measuring electrode form peeling. In addition, forming the upper layer on the lowermost layer, by using a material having a specific surface area larger than that of the lower most layer or a material having high adsorptivity for poisoning matter, can capture the poisoning matter in the gas to be measured, thereby protecting the measuring electrode. That is, as described above, the gas sensor element having excellent durability can be obtained by using the protective layer formed of at least two layers including the lower most layer for mainly controlling the diffusion of the gas to be measured and the upper layer for mainly capturing the poisoning matter.

In addition, the lower most layer of the protective layer which contacts the measuring electrode is preferably formed of a metallic oxide whose chief ingredient includes at least one of alumina, alumina magnesia spinel, and titanic.

In this case, since the metallic oxide is thermally and chemically stable, the protective layer can be obtained which is difficult to deteriorate even when exposed to the gas to be measured.

Note that, in the present description, the chief ingredient is defined as a metallic oxide whose content is more than 50% in the protective layer.

In addition, the gas sensor element preferably has a catalyst layer which covers the outer surface of the protective layer and is formed of a metallic oxide whose chief ingredient includes at least one of alumina, alumina magnesia spinel, and zirconia.

In this case, since the metallic oxide is thermally and chemically stable, the catalyst layer can be obtained which is difficult to deteriorate even when exposed to the gas to be measured.

First Embodiment

An embodiment of a gas sensor element and a gas sensor including the gas sensor element according to the present invention will be described with reference to FIGS. 1 to 7.

A gas sensor 1 of the embodiment includes, as shown in FIG. 1, a solid electrolytic substance 21 having a bottomed cylindrical shape and oxygen ion conductivity, a reference electrode 22 arranged on the inner side surface 212 of the solid electrolytic substance 21, a measuring electrode 23 arranged on the outer side surface 213 of the solid electrolytic substance 21, and a protective layer 24 which covers the outer side surface 213 of the solid electrolytic substance 21 together with the measuring electrode 23 and allows gas to be measured to pass through the protective layer 24.

The end side of the gas sensor element 2 is formed of, as shown in FIG. 1, a leg portion 202 whose profile line is straight on an axial cross section S, which is parallel to the axis of the gas sensor element 2, and a bottom portion 201 whose profile line is curved.

The film thickness of the protective layer 24 of the bottom portion 201 is larger than that of the protective layer 24 of the leg portion 202.

Hereinafter, a configuration of the gas sensor 1 will be described in detail.

Figure 2:
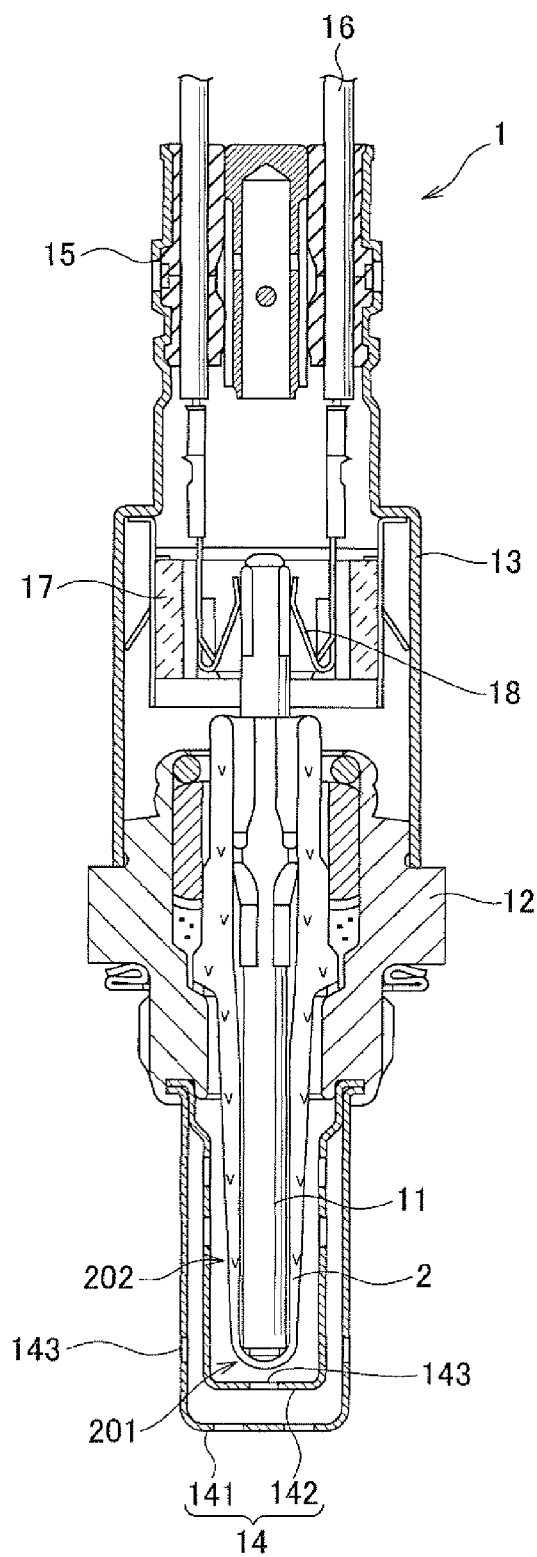
FIG. 2 is a sectional view of a gas sensor according to the first embodiment.

As shown in FIG. 2, the gas sensor 1 has, in addition to the gas sensor element 2, a heater 11, a housing 12, an atmosphere-side cover 13, and an element cover 14. The heater 11 is inserted inside the solid electrolytic substance 21 and produces heat by energization. The gas sensor element 2 is inserted inside the housing 12. The housing 12 holds the gas sensor element 2. The atmosphere-side cover 13 is arranged on the base side of the housing 12 and covers the base side of the gas sensor element 2. The element cover 14 is arranged on the end side of the housing 12 and covers the end side of the gas sensor element 2.

Furthermore, the gas sensor 1 has an atmosphere-side insulator 17, a bush 15, leads 16, and contact fittings 18. The atmosphere-side insulator 17 is arranged so as to cover the base side of the gas sensor element 2. The bush 15 is arranged on the base side of the atmosphere-side cover 13. The leads 16 are inserted inside the bush 15. The contact fittings 18 are connected to the leads 16 and electrically connected to the heater 11 and the gas sensor element 2.

The element cover 14 has, as shown in FIG. 2, gas introduction holes 143 in a bottom surface portion and a side surface portion thereof.

Specifically, the element cover 14 is a double cover in which an outer cover 141 and an inner cover 142 are caulked at the end portion of the housing 12.

The gas to be measured, which is introduced to a gap between the outer cover 141 and the inner cover 142 through the gas introduction holes 143 formed in the outer cover 141, is introduced inside the element cover 14 through the gas introduction holes 143 formed in the inner cover 142.

The inner cover 142 is formed with the gas introduction holes 143 which are positioned at the end side of the gas sensor 1 with respect to the protective layer 24 of the bottom portion 201.

Next, the gas sensor element 2 included in the gas sensor 1 will be described in detail.

The gas sensor element 2 is an A/F sensor element, which is included in an air-fuel ratio sensor disposed in an exhaust pipe of various internal combustion engines for vehicles and used for an exhaust gas feedback system, or an oxygen sensor element, which measures a concentration of oxygen in exhaust gas.

The gas sensor element 2 has, as described above, the solid electrolytic substance 21, the reference electrode 22, the measuring electrode 23, and the protective layer 24, as well as a catalyst layer 25 covering the outer surface of the protective layer 24 and a trap layer 26 covering the outer surface of the catalyst layer 25.

Specifically, the catalyst layer 25 consists of alumina particles carrying platinum and rhodium. The trap layer 26 consists of alumina particles. The catalyst layer 25 and the trap layer 26 are disposed on the outer side of the protective layer 24.

Note that the catalyst layer 25 and the trap layer 26 can be formed by using other than the alumina. The catalyst layer 25 and the trap layer 26 can be formed by using a metallic oxide whose chief ingredient includes at least one of alumina magnesia spinel and zirconia.

The catalyst layer 25 and the trap layer 26 can be formed by immersing the gas sensor element 2 or printing pastes forming the catalyst layer 25 and the trap layer 26 on the measuring electrode 23.

Figure 7:
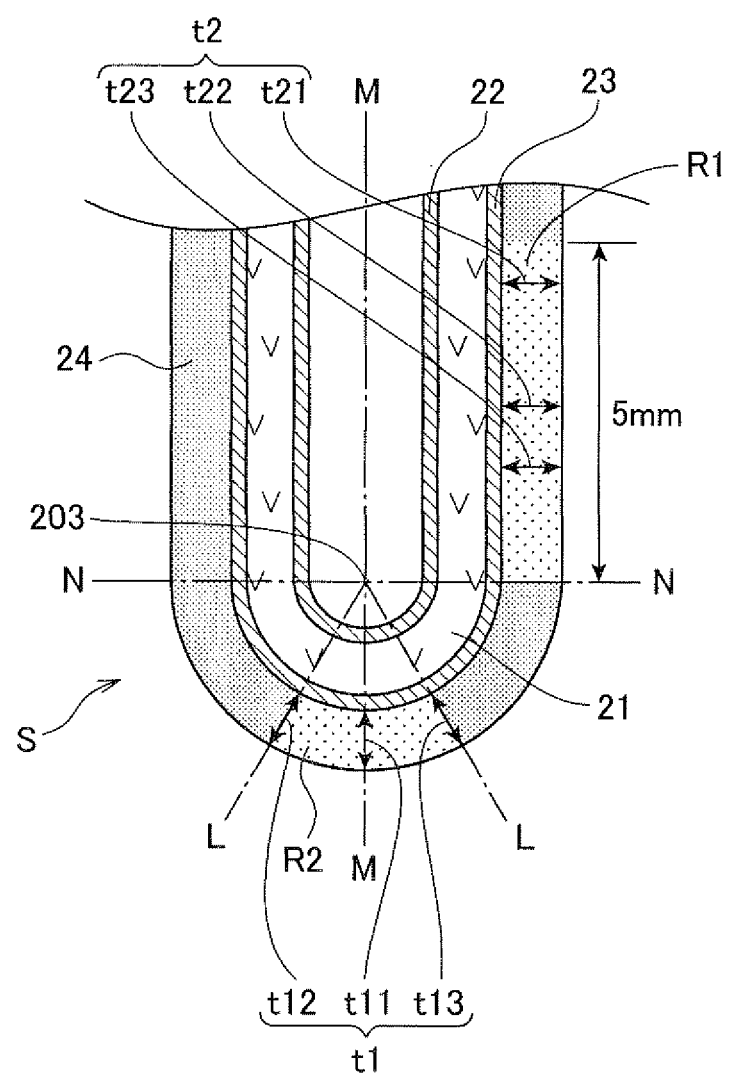
FIG. 7 is a drawing for explaining film thicknesses and porosities according to the first embodiment.

In the embodiment, as shown FIG. 7, film thickness t1 of the protective layer 24 of the bottom portion 201 is a value obtained by averaging film thicknesses at arbitrary three points described blow. That is, the film thickness t1 is a value obtained by averaging film thicknesses t11, t12, and t13 when viewing an axial cross section S. The film thickness t11 is a thickness of the protective layer 24 at a position where an axis M of the gas sensor element 2 passes through the bottom portion 201. The film thicknesses t12 and t13 are thicknesses of the protective layer 24 at two positions where lines L, L pass through the bottom portion 201. The lines L, L are inclined at an angle of 30° with respect to the axis M from the end side to the base side centering on a point 203 where a boundary N between the bottom portion 201 and the leg portion 202 and the axis M intersect with each other.

As shown FIG. 7, film thickness t2 of the protective layer 24 of the leg portion 202 is a value obtained by averaging film thicknesses at arbitrary three points described blow. That is, the film thickness t2 is a value obtained by averaging film thicknesses t21, t22, and t23 when viewing the axial cross section S. The film thicknesses t21, t22, and t23 are thicknesses of the protective layer 24 at arbitrary three positions in an area R1, whose length is 5 mm, extending from the boundary N toward the base side.

In the protective layer 24, a film thickness ratio of the film thickness t1 of the bottom portion 201 to the film thickness t2 of the leg portion 202 is 1.1 or more. More specifically, in the embodiment, the film thickness ratio is in the range of 1.2 to 2.

In the protective layer 24, the film thickness t1 of the bottom portion 201 may be in the range of 110 to 1000 μm, and the film thickness t2 of the leg portion 202 may be in the range of 100 to 500 μm.

Note that, in the gas sensor element 2 of the embodiment, the film thickness of the protective layer 24 of the bottom portion 201 is preferably in the range of 350 to 550 μm, and the film thickness of the protective layer 24 of the leg portion 202 is preferably in the range of 260 to 340 μm. In this case, response time of the sensor becomes short, and water resistance and strength can be improved.

Furthermore, in the protective layer 24, a porosity of the bottom portion 201 is higher than that of the leg portion 202. More specifically, in the protective layer 24, the porosity of the bottom portion 201 is 50% or less, and a porosity ratio, which is a ratio of the porosity of the bottom portion 201 to the porosity of the leg portion 202, is in the range of 1.1 to 10. In the embodiment, the porosity ratio of the protective layer 24 of the leg portion 202 is in the range of 2 to 20%. Therefore, the porosity ratio of the protective layer 24 of the bottom portion 201 can be in the range of 2.2 to 50%.

As described above, in the embodiment, in the protective layer 24, the porosity of the bottom portion 201 is higher than that of the leg portion 202. Note that it is more preferable that the porosity of the protective layer 24 of the bottom portion 201 is in the range of 8 to 20%, and the porosity of the protective layer 24 of the leg portion 202 is in the range of 3 to 7%.

In the embodiment, the porosity of the protective layer 24 is measured as below. The porosity of the protective layer 24 of the bottom portion 201 is a value obtained by averaging porosities at arbitrary three points in an area R2 of the protective layer 24 between two lines L, L. The lines L, L are inclined at an angle of 30° with respect to the axis M centering on a point 203 where the boundary N between the bottom portion 201 and the leg portion 202 and the axis M intersect with each other. As shown FIG. 7, the porosity of the protective layer 24 of the bottom portion 201 is a value obtained by averaging porosities at arbitrary three points in the area R1, whose length is 5 mm, extending from the boundary N toward the base side.

Although the protective layer 24 is formed of two layers in the above embodiment, the protective layer 24 may be formed of three or more layers or one layer.

When the protective layer 24 is formed of two or more layers, the undermost layer of the protective layer 24, which contacts the measuring electrode 23, preferably consists of a metallic oxide whose chief ingredient includes at least one of alumina, alumina magnesia spinel, and titania.

Next, a method of manufacturing the gas sensor element 2 will be described with reference to FIG. 3.

First, the measuring electrode 23 and the reference electrode 22 are applied to the outer side surface 213 and the inner side surface 212 of the solid electrolytic substance 21, respectively.

Next, the solid electrolytic substance 21, to which the measuring electrode 23 is applied as described above, is rotated on the axis M thereof. The gas sensor element 2 can be formed by spraying a protective material 4 described later to the rotating solid electrolytic substance 21. In this case, the gas sensor element 2 can be easily formed without using large equipment, which obtains an excellent gas sensor element.

Figure 3:
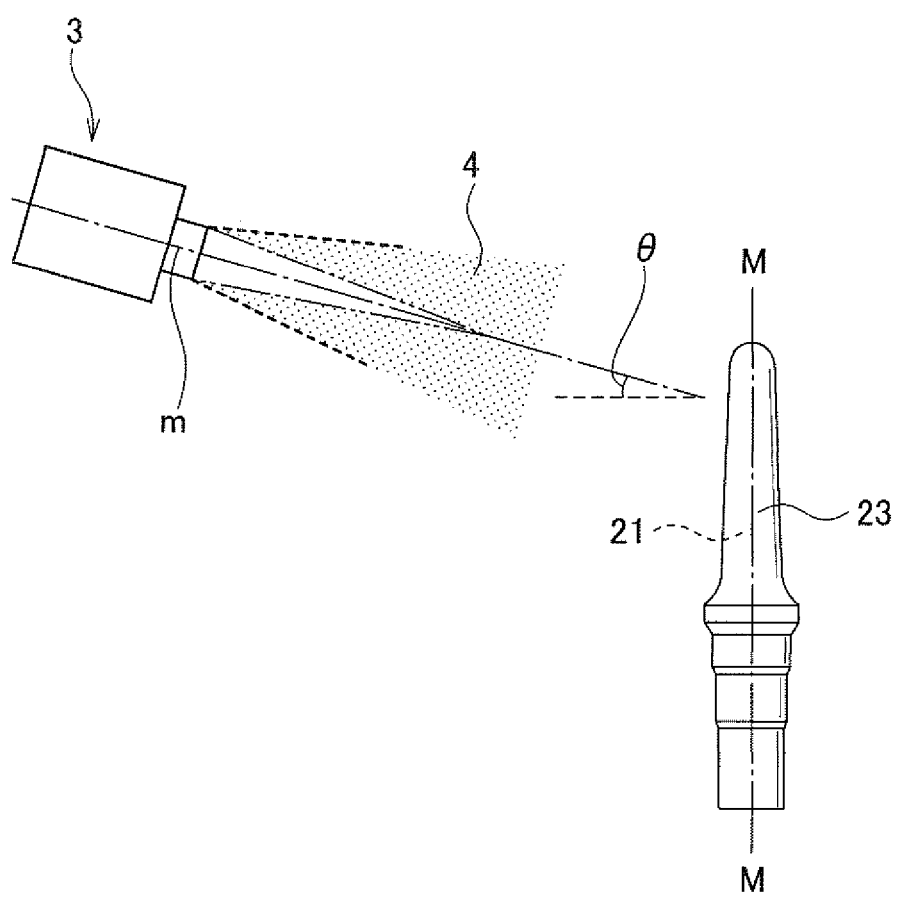
FIG. 3 is a drawing for explaining a thermal spraying process according to the first embodiment.

Furthermore, as shown in FIG. 3, the protective material 4 is sprayed on the measuring electrode 23 in a state where a spraying angle θ is less than 36° when assuming a direction inclined to an axial direction and the end side with respect to an orthogonal direction is the positive direction. The orthogonal direction is the direction orthogonal to the axial direction of the gas sensor element 2. That is, the protective material 4 is sprayed in a state where a thermal spraying gun 3, which sprays the protective material 4, is inclined at an angle of less than 36° with respect to the orthogonal direction.

The thermal spraying gun 3 has a nozzle electrode (not shown) which generates plasma, an inlet (not shown) through which orifice gas is injected, a spray outlet (not shown) through which the protective material 4 melted with the plasma is sprayed on the solid electrolytic substance 21, and a tank (not shown) in which spray powder (not shown) is stored.

In this case, the thermal spraying gun 3 consuming 35 kW of power can be used.

The distribution of the protective material 4 sprayed from the thermal spraying gun 3 is dense at a part near an axis m of the thermal spraying gun 3 and becomes less dense at angles farther from the axis m. In this case, when the spraying angle θ is set to less than 36°, the part of the protective material 4 whose distribution is non-dense is directed to the bottom portion 201. Therefore, the bottom portion 201 of the protective layer 24 which has relatively large film thickness and relatively high porosity can be formed. Meanwhile, the part of the protective material 4 whose distribution is dense is directed to the leg portion 202. Therefore, the leg portion 202 of the protective layer 24 which has relatively small film thickness and relatively low porosity can be formed.

Hereinafter, a thermal spraying process for forming the protective layer 24 will be described in detail.

First, the spray powder stored in the tank is supplied from the tank to the spray outlet through a feed pipe (not shown).

Next, the spray powder is melted with the plasma generated between the nozzle electrodes, thereby forming the protective material 4.

Next, the protective material 4 is sprayed on the solid electrolytic substance 21 with the plasma ejected from the spray outlet.

Then, in the thermal spraying process, the protective material 4 is sprayed so that the spraying angle θ becomes less than 36° as described above.

Specifically, when the protective material 4 is sprayed on the outer side surface 213 of the solid electrolytic substance 21 in a state where the spraying angle θ is more than 9° and less than 36°, the gas sensor element 2 is easily formed in which the film thickness of the protective layer 24 of the bottom portion 201 is larger than that of the leg portion 202. Consequently, as described later, the gas sensor element 2 having high water resistance can be easily obtained.

The thermal spraying gun 3 is preferably used at a distance of 50 to 150 mm from the end portion of the solid electrolytic substance 21.

In the embodiment, alumina whose average particle diameter is 30 μm or less is used as the spray powder. In this case, the protective layer 24 having desired porosity can be easily formed.

When the average particle diameter of the spray powder is more than 30 μm, the porosity becomes too high, and the water resistance and strength become low. This can easily crack the element.

Then, the protective material 4 is sprayed on the outer side surface 213 of the solid electrolytic substance 21 at a flow rate of 100 to 800 m/s in a state where the protective material 4 is melted at 1800 to 2200° C.

The thermal spraying process described above is completed.

Instead of the above process, as shown in FIG. 4, the spraying angle θ can be varied depending on a portion to be sprayed.

Figure 4A:
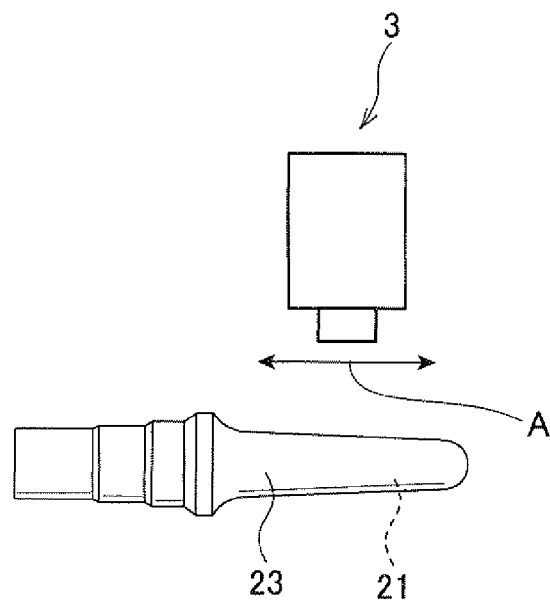
FIG. 4A is a drawing for explaining a state in which a leg portion is sprayed in another thermal spraying process.

When forming the protective layer 24 of the leg portion 202, the protective material 4 can be sprayed, as shown in FIG. 4A, in a state where the spraying direction is orthogonal to the axis of the gas sensor element 2, that is, the spraying angle θ is 0°, while moving the thermal spraying gun 3 (in the direction of an arrow A shown in FIG. 4A).

Figure 4B:
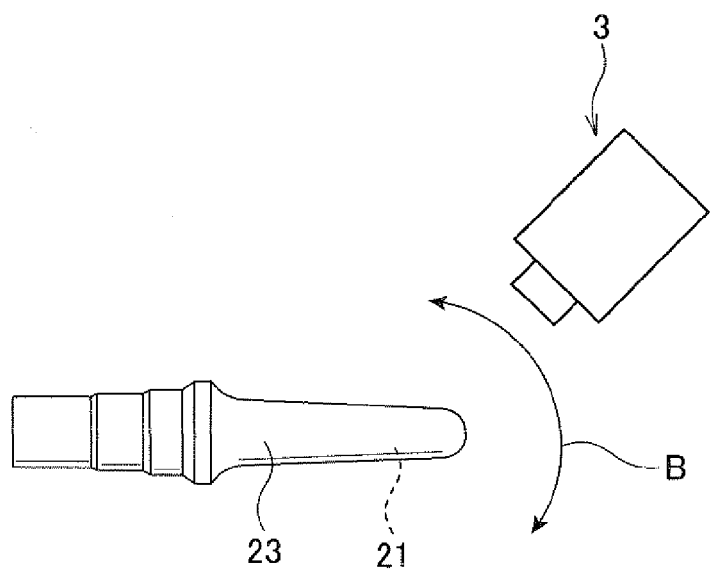
FIG. 4B is a drawing for explaining a state in which a bottom portion is sprayed in the thermal spraying process.

When forming the protective layer 24 of the bottom portion 201, the protective material 4 can be sprayed, as shown in FIG. 4B, while moving the thermal spraying gun 3 (in the direction of an arrow B shown in FIG. 4B).

The movements of the thermal spraying gun 3 (shown by the arrows A and B) may be made continuously or discontinuously. The bottom portion 201 may be subject to the spraying by the thermal spraying gun 3 exclusive to the bottom portion, and the leg portion 202 may be subject to the spraying by the thermal spraying gun 3 exclusive to the leg portion. Alternatively, the bottom portion 201 and the leg portion 202 may be subject to the spraying by the same thermal spraying gun 3.

Figure 5:
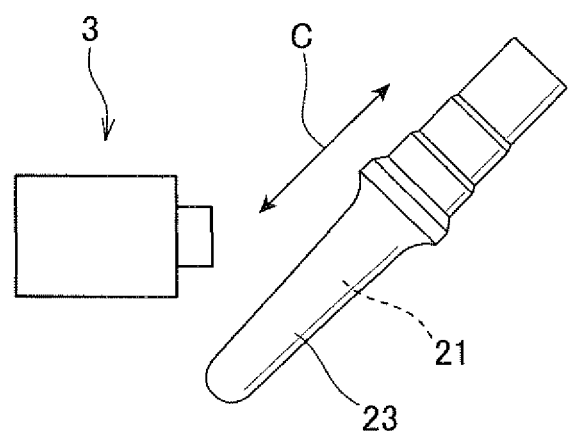
FIG. 5 is a drawing for explaining another thermal spraying process according to the first embodiment.

In addition, as shown in FIG. 5, the thermal spraying gun 3 may be fixed. In this case, the solid electrolytic substance 21 is moved (in the direction of an arrow C shown in FIG. 5) while rotating in a state where the solid electrolytic substance 21 is inclined with respect to the thermal spraying gun 3. This allows the solid electrolytic substance 21 to move toward or away from the thermal spraying gun 3.

As described above, the thermal spraying process can be realized by using various methods.

In the embodiment, the film thicknesses of the bottom portion 201 and the leg portion 202 can be controlled by adjusting the spraying angle θ, the movement distance of the thermal spraying gun 3, the rotation speed of the solid electrolytic substance 21, or the like.

In addition, after the thermal spraying process is completed, the film thickness of the protective layer 24 of the bottom portion 201 and the film thickness of the protective layer 24 of the leg portion 202 can be controlled by grinding the protective layer 24.

Next, the catalyst layer 25 is formed by immersing the solid electrolytic substance 21, in which the protective layer 24 is formed, in alumina slurry. The catalyst layer 25 can be formed by using slurry whose chief ingredient is alumina magnesia spinel or zirconia, instead of alumina.

Next, the trap layer 26 is formed on the surface of the protective layer 24 by immersing the solid electrolytic substance 21 in alumina slurry. The trap layer 26 can be also formed by using slurry whose chief ingredient includes alumina magnesia spinel or zirconia, in addition to alumina.

The gas sensor element 2 can be manufactured according to the above process.

Note that the form of the gas sensor element 2 is not limited to the form described above.

Figure 6A:
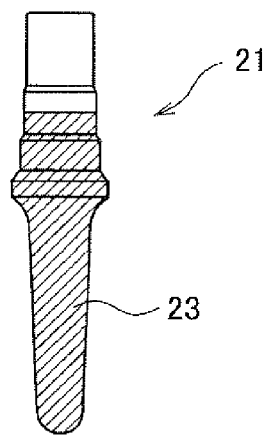
FIG. 6A is a side view of a measuring electrode according to the first embodiment.
Figure 6B:
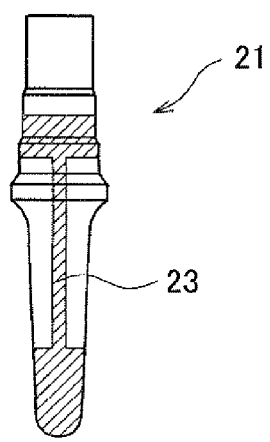
FIG. 6B is a side view of another measuring electrode according to the first embodiment.
Figure 6C:
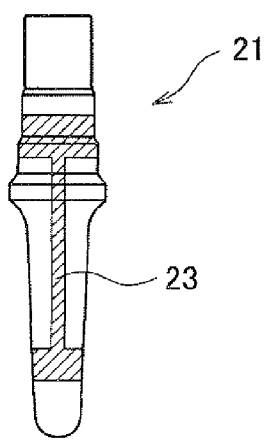
FIG. 6C is a side view of another measuring electrode according to the first embodiment.

In the above embodiment, as shown in FIG. 6A, the gas sensor element 2 has the measuring electrode 23 formed on substantially the whole of the outer side surface 213 of the solid electrolytic substance 21. However, as shown in FIG. 6B, the gas sensor element 2 may have the measuring electrode 23 locally formed on the outer side surface 213. Furthermore, as shown in FIG. 6C, the gas sensor element 2 may have the measuring electrode 23 which is not formed on the end side of the solid electrolytic substance 21.

Hereinafter, advantages of the embodiment will be described.

The film thickness of the protective layer 24 of the bottom portion 201 is larger than that of the protective layer 24 of the leg portion 202. In consequence, the gas sensor element 2 having high water resistance can be obtained. That is, immediately after the engine starts, water condensed on the element cover 14 covering the gas sensor element 2 easily contacts the bottom portion 201 of the solid electrolytic substance 21. Therefore, the bottom portion 201 is more easily cracked due to the is water than the leg portion 202. In addition, when water in the gas to be measured contacts the gas sensor element 2 when driving, the bottom portion 201, in which thermal stress is easily concentrated, is more easily cracked due to the water than the leg portion 202. That is, the bottom portion 201 of the solid electrolytic substance 21 has water resistance and strength lower than those of the leg portion 202 of the solid electrolytic substance 21.

Since the film thickness of the protective layer 24 of the bottom portion 201 is larger than that of the protective layer 24 of the leg portion 202, the bottom portion 201 of the solid electrolytic substance 21 covered with the protective layer 24 can be sufficiently prevented from getting wet directly.

In consequence, the gas sensor element 2 having high water resistance can be obtained.

In addition, for example, when the gas sensor element 2 is manufactured so that the film thickness of the protective layer 24 of the leg portion 202 is as large as that of the conventional one, and the film thickness of the protective layer 24 of the bottom portion 201 is as large as possible, responsiveness of the gas sensor element 2 can be improved compared with the gas sensor element in which the whole of the protective layer 24 is simply thickened. In addition, the amount of materials used for forming the protective layer 24 can be decreased. Therefore, the above gas sensor element 2 having excellent water resistance and responsiveness can be manufactured at low cost.

Furthermore, since the film thickness ratio of the protective layer is in the range of 1.2 to 2, the gas sensor element having sufficiently excellent water resistance and responsiveness can be obtained. In addition, when the protective layer is formed by thermal spraying, the solid electrolytic substance is prevented from cracking.

In addition, since the film thickness of the protective layer of the leg portion is in the range of 100 to 500 μm, the gas sensor element can is be obtained which has sufficient responsiveness as well as a function for protecting the electrodes by the protective layer.

In addition, in the protective layer 24, the porosity of the bottom portion 201 is 50% or less, and a porosity ratio, which is a ratio of the porosity of the bottom portion 201 to the porosity of the leg portion 202, is in the range of 1.1 to 10. Therefore, the protective layer 24 can be obtained which has sufficient strength as well as a function for protecting the electrodes. Furthermore, the gas sensor element 2 can be obtained which has sufficient responsiveness.

In addition, the porosity ratio of the protective layer 24 of the leg portion 202 is in the range of 2 to 20%. Therefore, the gas sensor element 2 can be obtained which ensures responsiveness, produces outputs with stability, and has the effect of sufficiently restricting passing gas to be measured.

In addition, since the protective layer 24 is formed of at least two layers, the gas sensor element 2 can be obtained which has excellent durability. That is, constructing the lower most layer densely allows the diffusion of the gas to be controlled, thereby obtaining a stable sensor characteristic, and prevents the measuring electrode 23 form peeling. In addition, forming the upper layer on the lower most layer, by using a material having a specific surface area larger than that of the lower most layer or a material having high adsorptivity for poisoning matter, allows the poisoning matter in the gas to be captured, thereby protecting the measuring electrode 23. That is, as described above, the gas sensor element 2 having excellent durability can be obtained by using the protective layer 24 formed of at least two layers including the lower most layer for mainly controlling the diffusion of the gas to be measured and the upper layer for mainly capturing the poisoning matter.

In addition, the lower most layer of the protective layer 24 which contacts the measuring electrode 23 is formed of a metallic oxide whose chief ingredient includes at least one of alumina, alumina magnesia spinel, and titanic. Since the metallic oxide is thermally and chemically stable, the protective layer 24 can be obtained which is difficult to deteriorate even when exposed to the gas to be measured.

The gas sensor element 2 has the catalyst layer 25 which covers the outer surface of the protective layer 24 and is formed of a metallic oxide whose chief ingredient includes at least one of alumina, alumina magnesia spinel, and zirconia. Since the metallic oxide is thermally and chemically stable, the catalyst layer 25 can be obtained which is difficult to deteriorate even when exposed to the gas to be measured.

Furthermore, the gas sensor 1 having excellent water resistance and responsiveness can be manufactured at low cost by using the above excellent gas sensor element 2.

As described above, according to the embodiment, the gas sensor element having excellent water resistance and responsiveness and the gas sensor using the gas sensor element can be provided at low cost Second Embodiment Following is an embodiment of a gas sensor element which is manufactured by changing the film thickness of the protective layer of the bottom portion and the film thickness of the protective layer of the leg portion. In the embodiment, water resistance of the gas sensor element is evaluated.

That is, samples of the gas sensor element are manufactured by changing the film thickness of the protective layer of the bottom portion in the range of 100 to 1000 μm and changing the film thickness of the protective layer of the leg portion in the range of 100 to 500 μm. The number of respective manufactured samples is four.

The porosities of the protective layer of the bottom portion and the leg portion are set to 5%, which is constant.

For each of the samples of the gas sensor element, in a state where the temperature thereof is set to 600° C., drops of water are dropped on the bottom portion and the leg portion. The amount of the drops of water is increased. When the element cracks, the amount of the drops of water is checked. Furthermore, the average value of the amounts of the drops of water of the respective samples is calculated.

In the embodiment, whether or not the element is cracked is determined by checking by insulation inspection whether or not the solid electrolytic substance is cracked. Specifically, after the test using water, the gas sensor element is immersed in a liquid including an alcohol aqueous solution. Thereafter, direct voltage is applied to the gas sensor element. Then, when the insulation is kept, it is determined that the gas sensor element is not cracked. Conversely, when the insulation is not kept, it is determined that the gas sensor element is cracked.

Then, for the samples whose film thicknesses of the protective layer of the leg portion are the same, the amounts of the drops of water for the bottom portion are evaluated. The following Table 1 shows the evaluation results. In Table 1, an x-mark is written for showing the case where the amount of the drops of water for the bottom portion is smaller than that for the leg portion, a circle is written for showing the case where the amount of the drops of water for the bottom portion is equivalent to that for the leg portion, and a double circle is written for showing the case where the amount of the drops of water for the bottom portion is larger than that for the leg portion.

TABLE 1

| | Film thickness (μm) | | | Amount of drops of water when the element is cracked (μL) | | |
|---|---|---|---|---|---|---|
| Sample No. | Bottom portion | Leg portion | Film thickness ratio | Bottom portion | Leg portion | Determination result |
| 1 | 100 | 100 | 1 | 3 | 4 | X |
| 2 | 110 | 100 | 1.1 | 4 | 4 | ◯ |
| 3 | 120 | 100 | 1.2 | 5 | 4 | ◎ |
| 4 | 130 | 100 | 1.3 | 5 | 4 | ◎ |
| 5 | 100 | 100 | 1.9 | 7 | 4 | ◎ |
| 6 | 200 | 100 | 2 | 7 | 4 | ◎ |
| 7 | 200 | 200 | 1 | 7 | 9 | X |
| 8 | 220 | 200 | 1.1 | 9 | 9 | ◯ |
| 9 | 240 | 200 | 1.2 | 10 | 9 | ◎ |
| 10 | 260 | 200 | 1.3 | 15 | 9 | ◎ |
| 11 | 380 | 200 | 1.9 | 25 | 9 | ◎ |
| 12 | 400 | 200 | 2 | 25 | 9 | ◎ |
| 13 | 300 | 300 | 1 | 15 | 20 | X |
| 14 | 330 | 300 | 1.1 | 20 | 20 | ◯ |
| 15 | 360 | 300 | 1.2 | 25 | 20 | ◎ |
| 16 | 390 | 300 | 1.3 | 25 | 20 | ◎ |
| 17 | 420 | 300 | 1.4 | 25 | 20 | ◎ |
| 18 | 450 | 300 | 1.5 | 30 | 20 | ◎ |
| 19 | 480 | 300 | 1.6 | 30 | 20 | ◎ |
| 20 | 510 | 300 | 1.7 | 30 | 20 | ◎ |
| 21 | 540 | 300 | 1.8 | 35 | 20 | ◎ |
| 22 | 570 | 300 | 1.9 | 40 | 20 | ◎ |
| 23 | 600 | 300 | 2 | 40 | 20 | ◎ |
| 24 | 400 | 400 | 1 | 25 | 30 | X |
| 25 | 440 | 400 | 1.1 | 30 | 30 | ◯ |
| 26 | 480 | 400 | 1.2 | 30 | 30 | ◎ |
| 27 | 520 | 400 | 1.3 | 40 | 30 | ◎ |
| 28 | 760 | 400 | 1.9 | 60 | 30 | ◎ |
| 29 | 800 | 400 | 2 | 60 | 30 | ◎ |

TABLE 1-continued

| | Film thickness (μm) | | | Amount of drops of water when the element is cracked (μL) | | |
|---|---|---|---|---|---|---|
| Sample No. | Bottom portion | Leg portion | Film thickness ratio | Bottom portion | Leg portion | Determination result |
| 30 | 500 | 500 | 1 | 30 | 40 | X |
| 31 | 550 | 500 | 1.1 | 40 | 40 | ○ |
| 32 | 600 | 500 | 1.2 | 40 | 40 | ⊚ |
| 33 | 650 | 500 | 1.3 | 60 | 40 | ⊚ |
| 34 | 950 | 500 | 1.9 | 70 | 40 | ⊚ |
| 35 | 1000 | 500 | 2 | 80 | 40 | ⊚ |

As can be understood from Table 1, when the film thickness of the protective layer of the bottom portion is equal to or larger than that of the leg portion (samples 2 to 6, 8 to 12, 14 to 23, 25 to 29, and 31 to 35 in Table 1), a circle or a double circle is written. Considering the film thickness ratios (film thickness of the bottom portion/film thickness of the leg portion) of these cases, when the film thickness ratio is 1.1 or more, water resistance and strength of the bottom portion can be improved. When the film thickness ratio is in the range of 1.2 to 2, water resistance and strength of the bottom portion can be further improved. In addition, the film thicknesses of the protective layer of the bottom portions of these cases are in the range of 100 to 500 μm.

On the other hand, when the film thickness of the protective layer of the bottom portion is smaller than that of the leg portion (samples 1, 7, 13, 24, and 30 in Table 1), the amount of the drops of water for the bottom portion is smaller than that for the leg portion when the element is cracked. That is, the bottom portion is cracked by the drops of water whose amount is smaller than that of the drops of water for the leg portion. Therefore, in this case, it can be understood that the bottom portion has insufficient water resistance and strength.

As can be understood from the above description, when the film thickness of the protective layer of the bottom portion is larger than that of the leg portion, water resistance and strength of the bottom portion can be improved.

In addition, when the film thickness ratio is in the range of 1.2 to 2, water resistance and strength of the bottom portion can be sufficiently heightened compared with those of the leg portion.

Furthermore, it can be understood that it is important that the film thickness of the protective layer of the leg portion is in the range of 100 to 500 μm, which improves the water resistance and strength.

Third Embodiment

Following is an embodiment of a gas sensor element which is manufactured by changing the porosity of the protective layer of the bottom portion and the porosity of the protective layer of the leg portion. In the embodiment, responsiveness of the gas sensor element is evaluated.

That is, samples of the gas sensor element are manufactured by changing the film thickness of the protective layer of the bottom portion in the range of 120 to 420 μm, changing the film thickness of the protective layer of the leg portion in the range of 100 to 300 μm, changing the porosity of the protective layer of the bottom portion in the range of 2 to 50%, and changing the porosity of the protective layer of the leg portion in the range of 2 to 20%.

Then, the responsiveness of each of the samples is evaluated

Specifically, the sensor output is checked while alternately supplying gases with rich atmosphere and lean atmosphere simulated for an actual vehicle. The period of the sensor output is measured as response time. The rich gas includes CO, $CH_4$, and $C_3H_8$ and is supplied so as to be λ=0.99. The lean gas includes $O_2$ and NO and is supplied so as to be λ=1.01.

For each of the groups of the samples (hereinafter, referred to as "category") whose protective layers of the bottom portions have equivalent film thickness and whose protective layers of the leg portions have equivalent film thickness and porosity, the difference in response time is checked with reference to the sample in which porosity of the protective layer of the bottom portion is equivalent to that of the protective layer of the leg portion. That is, for each category, responsiveness is evaluated with reference to the reference sample having the equivalent porosity. The following Table 2 shows the evaluation results. In the Table 2, a triangle is written for showing the case where the response time of the corresponding sample is longer than that of the reference sample (for which a hyphen is written), and a circle is written for showing the case where the response time of the corresponding sample is shorter than that of the reference sample.

TABLE 2

| | | Bottom portion | | Leg portion | | Responsiveness | |
|---|---|---|---|---|---|---|---|
| Category | Sample No. | Film thickness (μm) | Porosity (%) | Film thickness (μm) | Porosity (%) | Response time (min.) | Determination result |
| 1 | 1 | 420 | 4 | 300 | 5 | 1.9 | Δ |
| | 2 | 420 | 5 | 300 | 5 | 1.8 | — |
| | 3 | 420 | 5.5 | 300 | 5 | 1.7 | ○ |
| | 4 | 420 | 20 | 300 | 5 | 1.2 | ○ |
| | 5 | 420 | 50 | 300 | 5 | 1.0 | ○ |
| 2 | 6 | 420 | 2 | 300 | 2 | 2.4 | — |
| | 7 | 420 | 4 | 300 | 2 | 2.1 | ○ |
| 3 | 8 | 420 | 8 | 300 | 8 | 1.2 | — |
| | 9 | 420 | 16 | 300 | 8 | 0.9 | ○ |
| 4 | 10 | 420 | 11 | 300 | 11 | 0.9 | — |
| | 11 | 420 | 22 | 300 | 11 | 0.7 | ○ |
| 5 | 12 | 420 | 15 | 300 | 15 | 0.7 | — |
| | 13 | 420 | 30 | 300 | 15 | 0.5 | ○ |
| 6 | 14 | 420 | 20 | 300 | 20 | 0.5 | — |
| | 15 | 420 | 40 | 300 | 20 | 0.4 | ○ |
| 7 | 16 | 280 | 5 | 200 | 5 | 1.3 | — |

TABLE 2-continued

| Category | Sample No. | Bottom portion | | Leg portion | | Responsiveness | |
|---|---|---|---|---|---|---|---|
| | | Film thickness (μm) | Porosity (%) | Film thickness (μm) | Porosity (%) | Response time (min.) | Determination result |
| | 17 | 280 | 10 | 200 | 5 | 1.0 | ○ |
| 8 | 18 | 120 | 8 | 100 | 8 | 0.4 | — |
| | 19 | 120 | 16 | 100 | 8 | 0.3 | ○ |

As can be understood from Table 2, in all the categories, when porosity of the protective layer of the bottom portion is higher than that of the protective layer of the leg portion (samples 3 to 5, 7, 9, 11, 13, 15, and 19), response time is short compared with that of the reference sample. Therefore, circles are written as evaluation results.

Conversely, when porosity of the protective layer of the bottom portion is lower than that of the protective layer of the leg portion, response time is long compared with that of the reference sample. Therefore, a triangle is written as a evaluation result.

As can be understood from the above description, when the film thickness of the protective layer of the bottom portion is larger than that of the leg portion and the porosity of the protective layer of the bottom portion is higher than that of the leg portion, response time can be sufficiently shortened.

Furthermore, it can be understood that it is important that the porosity of the protective layer of the bottom portion is 50% or less, the porosity of the protective layer of the leg portion is in the range of 2 to 20%, and the porosity ratio is in the range of 1.1 to 10, which also improves the responsiveness.

Aspects of the above-described embodiments will then be summarized.

In order to achieve the object, the embodiments of the present invention provide, as one aspect, a gas sensor element including a solid electrolytic substance having a bottomed cylindrical shape and oxygen ion conductivity, a reference electrode arranged on an inner side surface of the solid electrolytic substance, a measuring electrode arranged on an outer side surface of the solid electrolytic substance, and a protective layer which covers the outer side surface of the solid electrolytic substance together with the measuring electrode and which allows gas to be measured to pass through the protective layer, wherein an end side of the gas sensor element is formed of a leg portion whose profile line is straight on an axial cross section, which is a cross section parallel to an axis of the gas sensor element, and a bottom portion whose profile line is curved, and the film thickness of the protective layer of the bottom portion is larger than the film thickness of the protective layer of the leg portion.

Hereinafter, advantages of the embodiments will be described.

The film thickness of the protective layer of the bottom portion is larger than that of the protective layer of the leg portion. In consequence, the gas sensor element having high water resistance can be obtained. That is, immediately after the engine starting, water condensed on the element cover covering the gas sensor element easily in contacts the bottom portion of the solid electrolytic substance. Therefore, the bottom portion is more easily cracked due to the water than the leg portion. In addition, when water in the gas to be measured contacts the gas sensor element when driving, the bottom portion, in which thermal stress is easily concentrated, is more easily cracked due to the water than the leg portion. That is, the bottom portion of the solid electrolytic substance has water resistance and strength lower than those of the leg portion of the solid electrolytic substance.

To solve the above problems, according to the embodiments, since the film thickness of the protective layer of the bottom portion is larger than that of the protective layer of the leg portion, the bottom portion of the solid electrolytic substance covered with the protective layer can be sufficiently prevented from getting wet directly.

In consequence, the gas sensor element having high water resistance can be obtained.

In addition, for example, when the gas sensor element is manufactured so that the film thickness of the protective layer of the leg portion is as large as that of the conventional one, and the film thickness of the protective layer of the bottom portion is as large as possible, responsiveness of the gas sensor element can be improved compared with the gas sensor element in which the whole of the protective layer is simply thickened. In addition, the amount of materials used for forming the protective layer can be decreased. Therefore, the above gas sensor element having excellent water resistance and responsiveness can be manufactured at low cost.

As described above, according to the embodiments of the embodiments, the gas sensor element can be provided which can be manufactured at low cost and has excellent water resistance and responsiveness.

In addition, the embodiments provide, as one aspect, a gas sensor which detects a concentration of specified gas to be measured, comprising the gas sensor element, a heater which is inserted inside the solid electrolytic substance and produces heat by energization, a housing inside which the gas sensor element is inserted, and which holds the gas sensor element, an atmosphere-side cover which is arranged on a base side of the housing and covers a base side of the gas sensor element, and an element cover which is arranged on an end side of the housing and covers an end side of the gas sensor element.

The gas sensor element included in the gas sensor can be manufactured at low cost and has excellent water resistance and responsiveness, as described above. Therefore, the gas sensor can be obtained which can be manufactured at low cost and has excellent water resistance and responsiveness.

It will be appreciated that the present invention is not limited to the configurations described above, but any and all modifications, variations or equivalents, which may occur to those who are skilled in the art, should be considered to fall within the scope of the present invention.

What is claimed is:

1. A gas sensor element including a solid electrolytic substance having a bottomed cylindrical shape and oxygen ion conductivity, a reference electrode arranged on an inner side surface of the solid electrolytic substance, a measuring electrode arranged on an outer side surface of the solid electrolytic substance, and a protective layer which covers the outer side surface of the solid electrolytic substance together with the measuring electrode and which allows gas to be measured to pass through the protective layer, wherein an end side of the gas sensor element is formed of a leg portion whose profile line is straight on an axial cross section, which is a cross section parallel to an axis of the gas sensor element, and a bottom portion whose profile line is curved, the film thickness of the protective layer of the bottom portion is larger than the film thickness of the protective layer of the leg portion, a porosity of the protective layer of the bottom portion is higher than that of the leg portion, the protective layer is formed of at least two layers, an undermost layer of the protective layer, which contacts the measuring electrode, includes a metallic oxide whose chief ingredient includes at least one of alumina, alumina magnesia spinel, and titania, and the gas sensor element further comprises a catalyst layer which covers an outer surface of the protective layer and is formed of a metallic oxide whose chief ingredient includes at least one of alumina, alumina magnesia spinel, and zirconia.

2. The gas sensor element according to claim 1, wherein the protective layer has a film thickness ratio of the film thickness of the bottom portion to the film thickness of the leg portion, the film thickness ratio being 1.1 or more.

3. The gas sensor element according to claim 2, wherein the film thickness ratio of the protective layer is in the range of 1.2 to 2.

4. The gas sensor element according to claim 1, wherein the film thickness of the protective layer of the leg portion is in the range of 100 to 500 µm.

5. The gas sensor element according to claim 1, wherein the porosity of the protective layer of the bottom portion is 50% or less, and a porosity ratio, which is a ratio of the porosity of the protective layer of the bottom portion to the porosity of the protective layer of the leg portion, is in the range of 1.1 to 10.

6. The gas sensor element according to claim 5, wherein the porosity ratio of the protective layer of the leg portion is in the range of 2 to 20%.

7. A gas sensor which detects a concentration of specified gas to be measured, comprising:

the gas sensor element according to claim 1;

a heater which is inserted inside the solid electrolytic substance and produces heat by energization;

a housing inside which the gas sensor element is inserted, and which holds the gas sensor element;

an atmosphere-side cover which is arranged on a base side of the housing and covers a base side of the gas sensor element; and an element cover which is arranged on an end side of the housing and covers an end side of the gas sensor element.

* * * * *